United States Patent
Dong et al.

(10) Patent No.: US 10,695,018 B2
(45) Date of Patent: Jun. 30, 2020

(54) TRAIN-LIKE PHARMACEUTICAL CONFIGURATION, APPARATUS FOR PREPARATION AND STORAGE DEVICE THEREOF

(71) Applicants: Yonghua Dong, Solon, OH (US); Rui Dong, Solon, OH (US)

(72) Inventors: Yonghua Dong, Solon, OH (US); Rui Dong, Solon, OH (US)

(73) Assignee: Medessence Lifesciences (Suzhou), Inc., Suzhou (CN)

( * ) Notice: Subject to any disclaimer, the term of this patent is extended or adjusted under 35 U.S.C. 154(b) by 0 days.

(21) Appl. No.: 16/483,441

(22) PCT Filed: Mar. 26, 2018

(86) PCT No.: PCT/US2018/024395
§ 371 (c)(1),
(2) Date: Aug. 4, 2019

(87) PCT Pub. No.: WO2018/183214
PCT Pub. Date: Oct. 4, 2018

(65) Prior Publication Data
US 2020/0008764 A1    Jan. 9, 2020

Related U.S. Application Data

(60) Provisional application No. 62/476,993, filed on Mar. 27, 2017.

(51) Int. Cl.
*A61B 6/00* (2006.01)
*A61B 8/08* (2006.01)
(Continued)

(52) U.S. Cl.
CPC ............... *A61B 6/481* (2013.01); *A61B 8/481* (2013.01); *A61B 17/12* (2013.01); *A61M 5/178* (2013.01);
(Continued)

(58) Field of Classification Search
CPC ......... A61B 6/481; A61B 8/481; A61B 17/12; A61M 5/178; A61M 25/00; A61M 2202/0225
See application file for complete search history.

(56) References Cited

U.S. PATENT DOCUMENTS 4,687,475 A    8/1987    Tai et al.
5,891,155 A    4/1999    Irie
(Continued)

FOREIGN PATENT DOCUMENTS

WO    2016001378 A1    1/2016

OTHER PUBLICATIONS

Cho, Kyung Jae, Carbon Dioxide Angiography: Scientific Principles and Practice, 2015, Vascular Specialist International, vol. 31, No. 3, pp. 67-80. (Year: 2015).*

(Continued)

*Primary Examiner* — Trevor Love
(74) *Attorney, Agent, or Firm* — Guosheng Wang; United States Research and Patent Firm

(57) ABSTRACT

The present invention provides a train-like pharmaceutical composition (configuration, or dosage form) comprising segments linearly arranged in series like cars of a train. When the pharmaceutical composition is administrated into a patient's body, some of the segments are "visible" to an instrument, but others are not. However, "invisible" segments can be estimated, deduced, calculated, or inferred from "visible" segments. The "invisible" segments can be used for neutralizing intratumoral lactic acidosis combined (Continued)

with glucose deprivation to control tumor, among other applications.

11 Claims, 6 Drawing Sheets

(51) Int. Cl.
    *A61B 17/12*     (2006.01)
    *A61M 5/178*     (2006.01)
    *A61M 25/00*     (2006.01)

(52) U.S. Cl.
    CPC ..... *A61M 25/00* (2013.01); *A61M 2202/0225* (2013.01)

(56) References Cited

U.S. PATENT DOCUMENTS

| | | |
|---|---|---|
| 6,344,027 B1 | 2/2002 | Goll |
| 2011/0264073 A1 | 10/2011 | Cragg et al. |
| 2016/0256501 A1 | 9/2016 | Sultan et al. |

OTHER PUBLICATIONS

Written Opinion of International Search Authority (USPTO) for PCT Application No. PCT/US18/24395, dated Jun. 20, 2018.
Revskaya, E et al. A Radiolabeled Fully Human Antibody to Human Aspartyl (Asparaginyl) b-Hydroxylase Is a Promising Agent for Imaging and Therapy of Metastatic Breast Cancer; Cancer Biotherapy and Radiopharmaceuticals, vol. 32, No. 2, pp. 57-65; Mar. 1, 2017.

\* cited by examiner

TRAIN-LIKE PHARMACEUTICAL CONFIGURATION, APPARATUS FOR PREPARATION AND STORAGE DEVICE THEREOF

CROSS-REFERENCE TO RELATED APPLICATIONS

This application expressly claims all Paris Convention and related priority from U.S. Provisional Application for U.S. Patent Ser. No. 62/476,993 titled "Train-Like Pharmaceutical Configuration and Method Thereof" and filed Mar. 27, 2017, which is incorporated by references as if set forth in its entirety.

FIELD OF THE INVENTION

The present invention generally relates to a train-like pharmaceutical composition (configuration, or dosage form), a medical apparatus for preparing the pharmaceutical composition, and a medical storage device for sealing and storing the pharmaceutical composition. Although the invention will be illustrated, explained and exemplified by releasing the train-like pharmaceutical composition into a blood vessel lumen for the purpose of diagnosis and therapy e.g. embolism and cancer treatment, such as neutralizing intratumoral lactic acidosis combined with glucose deprivation to control tumor; it should be appreciated that the present invention can also be applied to other fields.

BACKGROUND OF THE INVENTION

Sclerotherapy is a procedure used to treat blood vessels or blood vessel malformations (vascular malformations) and also those of the lymphatic system. Sclerosis is the thickening of the vessel wall and sealing off the blood flow. In foam sclerotherapy, "foamed sclerosant drugs" are injected into a blood vessel using a pair of syringes, one with sclerosant in it and one with gas such as air. The sclerosant drugs such as sodium tetradecyl sulfate or polidocanol are mixed with air or a physiological gas (e.g. carbon dioxide) in a syringe or by using mechanical pumps.

For example, arteriovenous malformation (AVM) is an abnormal connection between arteries and veins, bypassing, the capillary system. Ethanol is a sclerosing agent very good for treating AVM. Ethanol will harden the endothelial lining of vessels, denature proteins of the endothelium, and activate the coagulation system to cause a blood clot. However, in X-ray imaging guided sclerotherapy, ethanol administration is not easy to monitor and control. Therefore, ethanol injected into a patient's body may be out of control and flow to an area that causes damage to the tissue in the area.

Therefore, there exists a need to overcome the aforementioned problems, as well as a need to conveniently and precisely delivery basic chemical agents to a tumor for neutralizing intratumoral lactic acidosis combined with glucose deprivation of that tumor. Advantageously, the present invention provides train-like pharmaceutical composition (configuration, or dosage form) which exhibits numerous technical merits such as precise control of "invisible" chemical agent inside a patient's body, maximal and safe tumor control and sclerosant action, among others.

SUMMARY OF THE INVENTION

One aspect of the present invention provides a train-like pharmaceutical composition (configuration, or dosage form) comprising, a head segment and a body segment linearly arranged in series like two adjacent cars of a train. When the pharmaceutical composition is administrated into a patient's body, the head segment's location can be observed by a human with the aid of an instrument. However, the body segment's location cannot be observed by a human with the aid of the same instrument. With the present invention, the body segment's location can be estimated, deduced, calculated, or inferred based on the observed head segment's location.

Another aspect of the invention provides a medical apparatus for assembling and delivering the train-like pharmaceutical composition as described above into a blood vessel lumen. The apparatus includes at least (1) a head segment material source, (2) a head material tube (such as a channel within a catheter) for delivering the head segment material from said head segment material source directly into the blood vessel lumen, (3) a body segment material source, and (4) a body material tube (such as a channel within a catheter) for delivering the body segment material from said body segment material source directly into the blood vessel lumen.

Still another aspect of the invention provides a medical storage device comprising a tube for storing the train-like pharmaceutical composition as described above.

A further aspect of the invention provides a method of treating a blood vessel and cells around the blood vessel. The method comprises (i) providing the train-like pharmaceutical composition as described above; (ii) administrating the pharmaceutical composition into a patient's body; (iii) observing the head segment's location with the raid of an instrument; and (iv) estimating, deducing, calculating or inferring the body segment's location based on the observed head segment's location, wherein the body segment's location cannot be directly observed by a human with the aid of the same instrument.

The above features and advantages and other features and advantages of the present invention are readily apparent from the following detailed description of the best modes for carrying out the invention when taken in connection with the accompanying drawings.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements. All the figures are schematic and generally only show parts which are necessary in order to elucidate the invention. For simplicity and clarity of illustration, elements shown in the figures and discussed below have not necessarily been drawn to scale. Well-known structures and devices are shown in simplified form, omitted, or merely suggested, in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Where a numerical range is disclosed herein, unless otherwise specified, such range is continuous, inclusive of both the minimum and maximum values of the range as well as every value between such minimum and maximum values. Still further, where a range refers to integers, only the integers from the minimum value to and including the maximum value of such range are included. In addition, where multiple ranges are provided to describe a feature or characteristic, such ranges can be combined.

It is also to be understood that the terminology used herein is for the purpose of describing particular embodiments only, and is not intended to limit the scope of the invention. For example, when an element is referred to as being "on", "connected to", or "coupled to" another element, it can be directly on, connected or coupled to the other element or intervening elements may be present. In contrast, when an element is referred to as being "directly on", "directly connected to", or "directly coupled to" another element, there are no intervening elements present.

Figure 1:
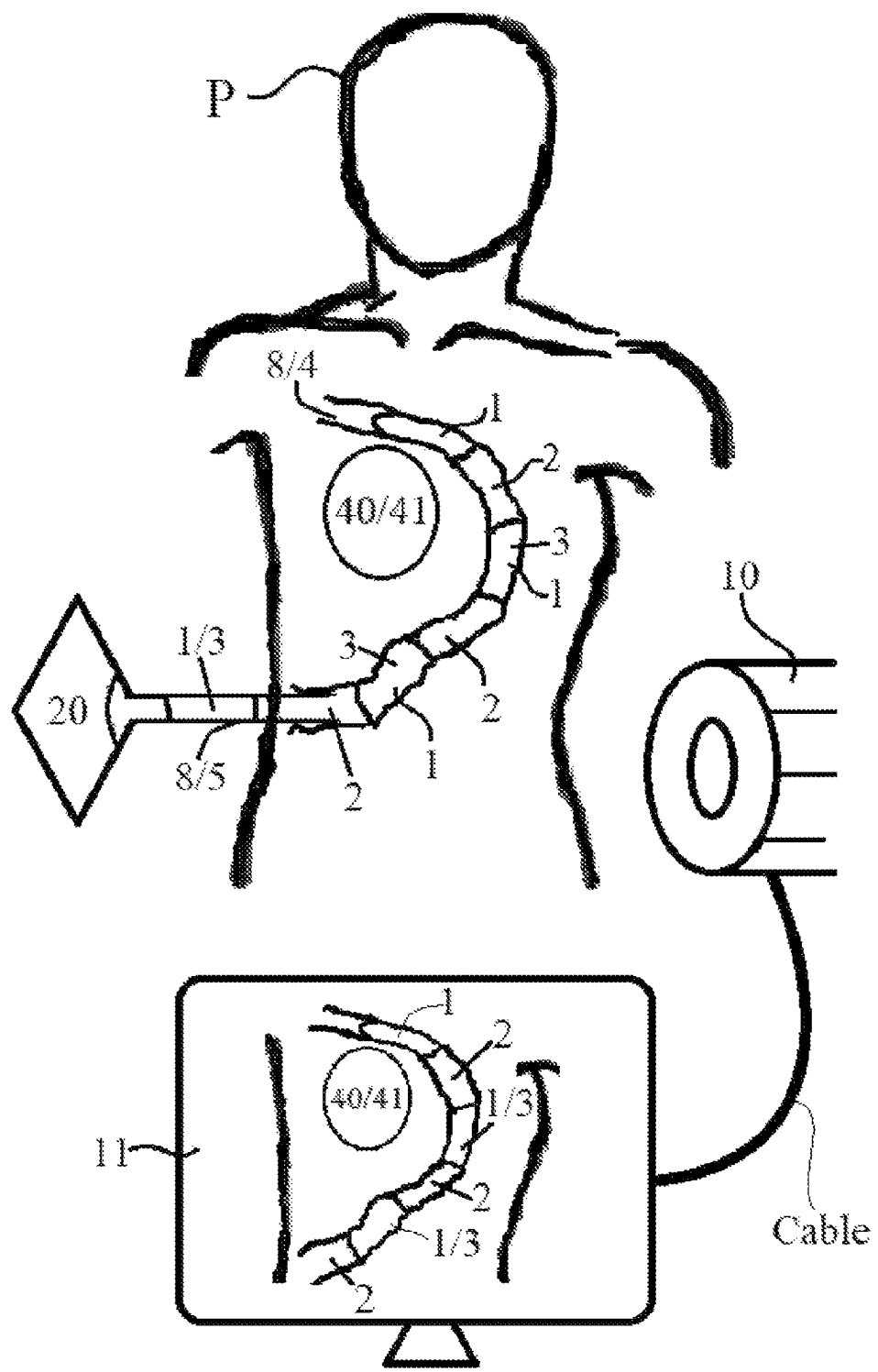
FIG. 1 schematically shows a train-like pharmaceutical composition being administrated into a patient in accordance with an exemplary embodiment of the present invention.

As shown in FIG. 1, a train-like pharmaceutical composition includes a head segment 1 and a body segment 2 linearly arranged in series like two adjacent cars of a train. The pharmaceutical composition may be alternatively named as a train-like pharmaceutical configuration, or a train-like pharmaceutical dosage form. When the pharmaceutical composition is administrated into a patient P's body, the location of the head segment 1 can be observed (e.g. on a display 11) by a human with the aid of an instrument 10. However, the location of the body segment 2 cannot be observed, or cannot be observed sufficiently clearly, by a human with the aid of the same instrument 10. According to the invention, the location of body segment 2 can be estimated or deduced from the observed location of head segment 1. The train-like pharmaceutical composition may further include a tail segment 3 that can be observed by a human with the aid of the instrument 10. The body segment 2 is sandwiched between the head segment 1 and the tail segment 3. The head segment 1, the body segment 2 and the tail segment 3 are linearly arranged in series like three consecutive cars of a train. Therefore, the location of the body segment 2 can be estimated or deduced from the observed head segment 1's location and/or tail segment 3's location.

The arrangement of head segment 1 and body segment 2 as described above can be repeated for one or more times to form a (body-head)$_n$ configuration or simply (B-H)$_n$ configuration. B or body stands for body segment 2; H or head stands for head segment 1; and n is an integer and n≥2. As a result, 2n head/body segments in total may be arranged in series like 2n consecutive cars of a train. In some embodiments, this train-like pharmaceutical composition may further include one more tail segment 3 that can be observed by a human with the aid of instrument 10, to form a tail-(body-head)n configuration or simply T-(B-H)$_n$ configuration, wherein T or tail stands for tail segment; n is an integer and n≥2. As a result, 2n+1 head/body/tail segments arranged in series like 2n+1 consecutive cars of a train. As shown in FIG. 1, a segment 1/3 located between two body segments 2 can be viewed as the tail segment 3 of the front body segment 2, or viewed as the head segment 1 of the following body segment 2.

In preferred embodiments, the first segment of the train-like pharmaceutical composition that is entered into or administrated into the patient's body is preferably a head segment 1. In other words, the first car of the train is preferably a head segment. In rare situations, the first car of the train can be a body segment.

As shown in FIG. 1, the train-like pharmaceutical composition may be confined within a lumen of a tubular structure 8 having an elongation direction, like a train is confined within a tunnel. Tubular structure 8 can be a blood vessel 4 of a human or an animal, a catheter 5, or a combination thereof. By "combination", it is intended to mean that the catheter 5 is inserted into the blood vessel 4 and their lumens are connected, joined, combined, or extended from one into another, so as to constitute a continuous passageway for the pharmaceutical composition to move through. Examples of blood vessel 4 include, but are not limited to, an arteriole, or a blood vessel between an arteriole and its downstream capillaries supplying blood to target cells 40 such as tumor cells 41. As will be described in details, a medical apparatus 20 may be used for assembling and delivering the train-like pharmaceutical composition into a blood vessel lumen. The lumen of tubular structure 8, either blood vessel 4 or catheter 5, has an internal diameter (or an internal maximal dimension) at a position of the lumen, and any segment 1/2/3 (head, body, or tail) that is confined at said position has a diameter (or an external maximal dimension) same as said internal diameter (or said internal maximal dimension). In other words, segment 1/2/3 at the position fill up the entire space of the lumen at that position. For a given volume of segment 1/2/3, when the lumen is larger at a position, corresponding segment 1/2/3 at that position will have a larger diameter, but a smaller length along the elongation direction of the lumen.

Examples of instrument 10 include, but are not limited to, an X-ray-based imaging apparatus used in computed tomography (CT), radiography, and fluoroscopy; an ultrasound apparatus; a magnetic resonance imaging (MRI) apparatus; or any combination thereof.

Head segment 1, body segment 2 and tail segment 3 may be independently of each other in the form of gas, liquid, slurry, or solid, as long as the body segment 2 is not completely dissolved, dispersed or suspended into head segment 1 or tail segment 3. For example, the head segment 1 and the tail segment 3 may be independently of each other a gas such as carbon dioxide, air, nitrogen, oxygen, inert gases, or mixture thereof; a solution (e.g. water solution) of an iodinated contrast agent such as ionic compounds e g. diatrizoate, metrizoate, iothalamate and ioxaglate; non-ionic compounds e.g.iopamidol, ioxilan, iopromide, iodixanol and, ioversol; or any mixture thereof. Such pharmaceutical composition of the invention may be injected as a radio-opaque or radio-transparent contrast agent into the blood vessel for imaging technique using X-ray based techniques such as fluoroscopy. Angiography or arteriography is a medical imaging technique used to visualize the inside, or lumen, of blood vessels and organs of the body, with particular interest in the arteries, veins, and the heart chambers.

Such pharmaceutical composition of the invention may be used as radiocontrast agents, a type of medical contrast medium used to improve the visibility of internal bodily structures in X-ray-based imaging techniques such as computed tomography (CT), radiography, and fluoroscopy. The train-like pharmaceutical configuration of the invention may include iodine or barium compounds and it improves visibility of an area, known as "contrast enhancing".

Carbon dioxide is commonly used in angiography. $CO_2$ angiography can be widely used for vascular imaging and endovascular procedures. $CO_2$ is low-risk as it is a natural product with no risk of allergic potential. However, it is preferably used below the diaphragm as there is a risk of embolism in neurovascular procedures. $CO_2$ is a negative contrast agent in that it displaces blood when injected intravascularly. Carbon dioxide ($CO_2$) gas can also be used as a contrast agent in the venous circulation to delineate the right heart for evaluation of suspected pericardial effusion. $CO_2$ is safe and well tolerated with peripheral venous injections. $CO_2$ can be used as an intra-arterial contrast agent. With digital subtraction angiography (DSA), $CO_2$ angiography is a useful diagnostic tool, particularly in patients who were hypersensitive to iodinated contrast material or whose renal function was compromised. Moreover, $CO_2$ can be used to guide various vascular interventions, including angioplasty and stent placement, transcatheter embolization, and endovascular abdominal aortic aneurysm (AAA) repair, Since $CO_2$ is approximately 20 times more soluble than oxygen, the volume of the gas needs to be adjusted as needed. When injected into a vessel, $CO_2$ bubbles completely dissolve within 2-3 minutes; therefore a larger volume of $CO_2$ will be needed. If the gas is trapped in a large abdominal aneurysm, it may persist, allowing gas exchange between the $CO_2$ and nitrogen in the blood, therefore a smaller volume of $CO_2$ will be needed. This exchange may result in colonic ischemia, as a result of occlusion of the inferior mesenteric artery. The localized accumulation of gas bubbles may produce a significant gas embolism, particularly in the pulmonary artery.

In some embodiments, the head/tail segment 1/3 is a gas such as carbon dioxide, and the body segment 2 is a liquid, Preferred examples of the liquid include alcohols such as pure ethanol, or ethanol that contains a minimal amount of water, such as less than 1%, 0.1%, or 0.01% of water by weight. It should be appreciated that, when ethanol contacts a human or animal tissue, more or less additional body fluid with water may be introduced into ethanol Ethanol may have a volume of 0.0001~1 milliliter.

A therapeutic agent such as a basic substance or basic compound may be dissolved, suspended, or dispersed in ethanol. The ethanol may be alkalized. Examples of the basic substance or alkaline agent include, but are not limited to, sodium ethoxide, sodium carbonate, sodium hydrogen carbonate, sodium hydroxide, potassium ethoxide, potassium carbonate, potassium hydrogen carbonate, potassium hydroxide, primary amine, secondary amine, tertiary amine, aliphatic amine, aromatic amine, and the like. The basic substance can be present in ethanol in an amount of 0.01-20% or even higher by weigh of the ethanol, depending on the applications and, strength of the basic substance, e.g. basicity. When $CO_2$ is injected into the blood, it is combined with water to produce carbonic acid. As such, there is a possibility that carbonic acid can neutralize the basic substance in ethanol. This should be taken into consideration as a factor, and more amount of basic substance should be included in ethanol to compensate such "loss" by $CO_2$ neutralization.

The basic substance can be used to kill cancerous cells 40/41. For example, neutralizing intratumoral lactic acidosis combined with glucose deprivation may deliver an effective approach to control tumor. Patients may be treated with transarterial chemoembolization (TACE) with local infusion of the basic substance into tumor. TACE is a minimally invasive procedure performed in interventional radiology to restrict a tumor's blood supply. It combines chemotherapy with embolization (chemoembolization). For example, small embolic particles coated with chemotherapeutic drugs are injected selectively through a catheter into an artery directly supplying the tumor. These particles both block the blood supply and induce cytotoxicity, attacking the tumor in several ways. The basic ethanol in the body segment 2 of the invention functions similarly to such embolic particles, except it is for neutralizing intratumoral lactic acidosis combined with glucose deprivation.

In the cancer management application, the train-like composition of the invention ($CO_2$ and/or ethanol) can function as an embolus, besides blocking the blood supply to the tumor, also includes an ingredient such as the basic substances to attack the tumor chemically.

It should be appreciated that body segment 2 (e.g. ethanol) may carry any suitable chemotherapy drug to preform chemoembolization such as TACE Body segment 2 may alternatively or additionally carry a radiopharmaceutical for unsealed source radiotherapy such as radioembolization or selective internal radiation therapy (SIRT). Embolization is a minimally invasive surgery that can prevent blood flow to an area of the body, and effectively shrink a tumor or block an aneurysm. The procedure is typically carried out as an endovascular procedure by a radiologist in an interventional suite.

Figure 2:
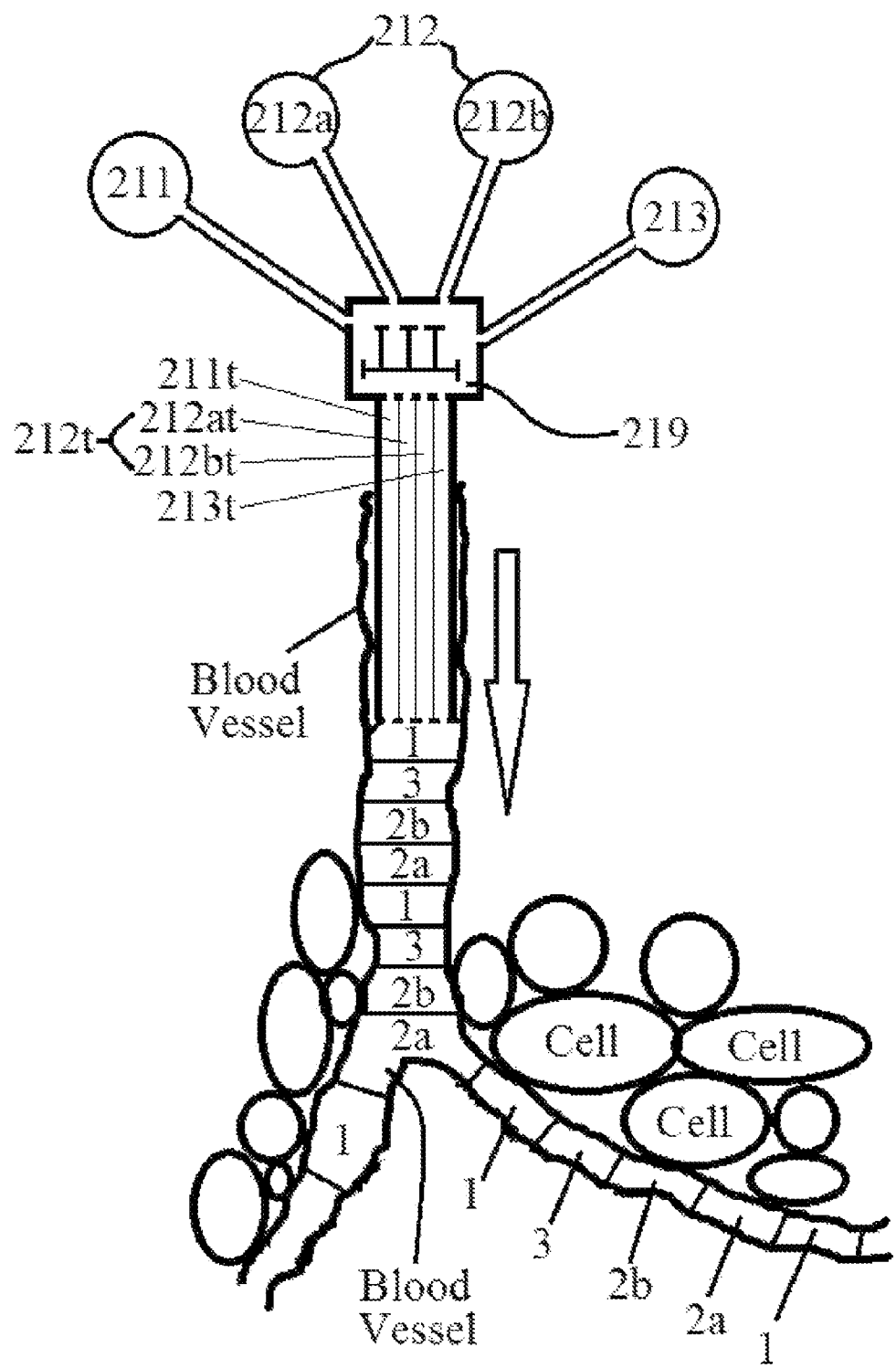
FIG. 2 schematically illustrates a first design of a medical apparatus for assembling and delivering the train-like pharmaceutical composition into a blood vessel lumen in accordance with an exemplary embodiment of the present invention.

FIG. 2 schematically shows an exemplary medical apparatus 21 for assembling and delivering the train-like pharmaceutical composition of the invention into a blood vessel lumen Access to the organ under treatment may be acquired by means of a guidewire and catheter(s). The position of the correct artery or vein supplying the pathology in question is located by digital subtraction angiography (DSA) These images are then used as a map for the radiologist to gain access to the correct vessel by selecting an appropriate catheter and/or wire, depending on the "shape" of the surrounding anatomy. Once the artificial emboli of the present invention have been successfully introduced, another set of DSA images may be taken to confirm a successful deployment, except $CO_2$ that does not need this.

Medical apparatus 21 includes ahead segment material source 211. A head material tube 211t, such as a channel within a catheter, is employed for delivering the head segment material 1 from said head segment material source 211 directly into the blood vessel lumen. Similarly, a body material tube 212t, such as a channel within a catheter, is employed for delivering body segment material 2 from a body segment material source 212 directly into the blood vessel lumen.

For example, head segment material source 211 may be a CO2 source in the form of a tank or cylinder, filled with 99.99% laboratory-grade CO2 The cylinder may be supplied with highly pure gas, a valve, a regulator, a gas gauge, and a metal diaphragm with the regulator set at 18 psi. Because of the risk of injection of large volumes of CO2, the catheter should not be directly connected to the CO2 cylinder, which contains a large volume of CO2 at very high pressure. In a manual mode, CO2 may be delivered into a vessel using e.g. a handheld syringe, by a plastic bag system. The plastic bag may be connected to the carbon dioxide cylinder through a 0.2 micrometer filter. A 3-way stopcock between the cylinder and the bag allows filling and emptying of the bag with carbon dioxide to remove residual air from the bag.

When a syringe is used, it is preferably filled directly from a CO2 cylinder. Sometimes, CO2 should not be aspirated into the syringe because this may cause air contamination. When the syringe has been filled with CO2, its pressure should be reduced to the atmospheric level by quickly opening and closing the stopcock. The CO2-filled syringe should not be left on the table with the stopcock open before injection, because the CO2 in the syringe (which has a CO2 concentration of >99%) is rapidly replaced with air (which has a CO2 concentration of only 0.03%).

The CO2 injection rate depends on the diameter, length, and flow of the blood vessels being imaged or treated. For an abdominal aortogram or an inferior vena cavogram, 30-40 cc of CO2 may be injected. When imaging aortic branches (celiac, superior mesenteric, renal arteries) or arteries of the lower extremity, 20-30 cc may be used, Because of the low viscosity of the gas, CO2 may be injected through a 3-Fr microcatheter for selective and superselective angiography and for selective arterial embolization.

Sometimes, the body segment material 2 is produced in situ by mixing two materials 2a and 2b. Then, two body material tubes 212at and 212bt, such as two channels within a catheter, are employed for delivering body segment materials 2a and 2b from body segment material sources 212a and 212b directly into the blood vessel lumen. Two materials 2a and 2b may be miscible or immiscible, and therefore, body segment 2 may be made of a homogeneous material, or it may be divided into two sub-segments 2a and 2b. If desired, a tail material tube 213t, such as a channel within a catheter, may be employed for delivering tail segment material 3 from a tail segment material source 213 directly into the blood vessel lumen. A controller 219 controls the time (timing) and amount of materials 1, 2a, 2b and 3 delivered into the blood vessel lumen so that the segments are linearly arranged in series in the blood vessel lumen like many cars of a train, >>> . . . 3-2b-2a-1-3-2b-2a-1-3-2b-2a-1>>>, >>> . . . 3/1-2b-2a-3/1-2b-2a-3/1-2b-2a-1>>>, or >>> . . . 3/1-2-3/1-2-3/1-2-1>>>.

Figure 3:
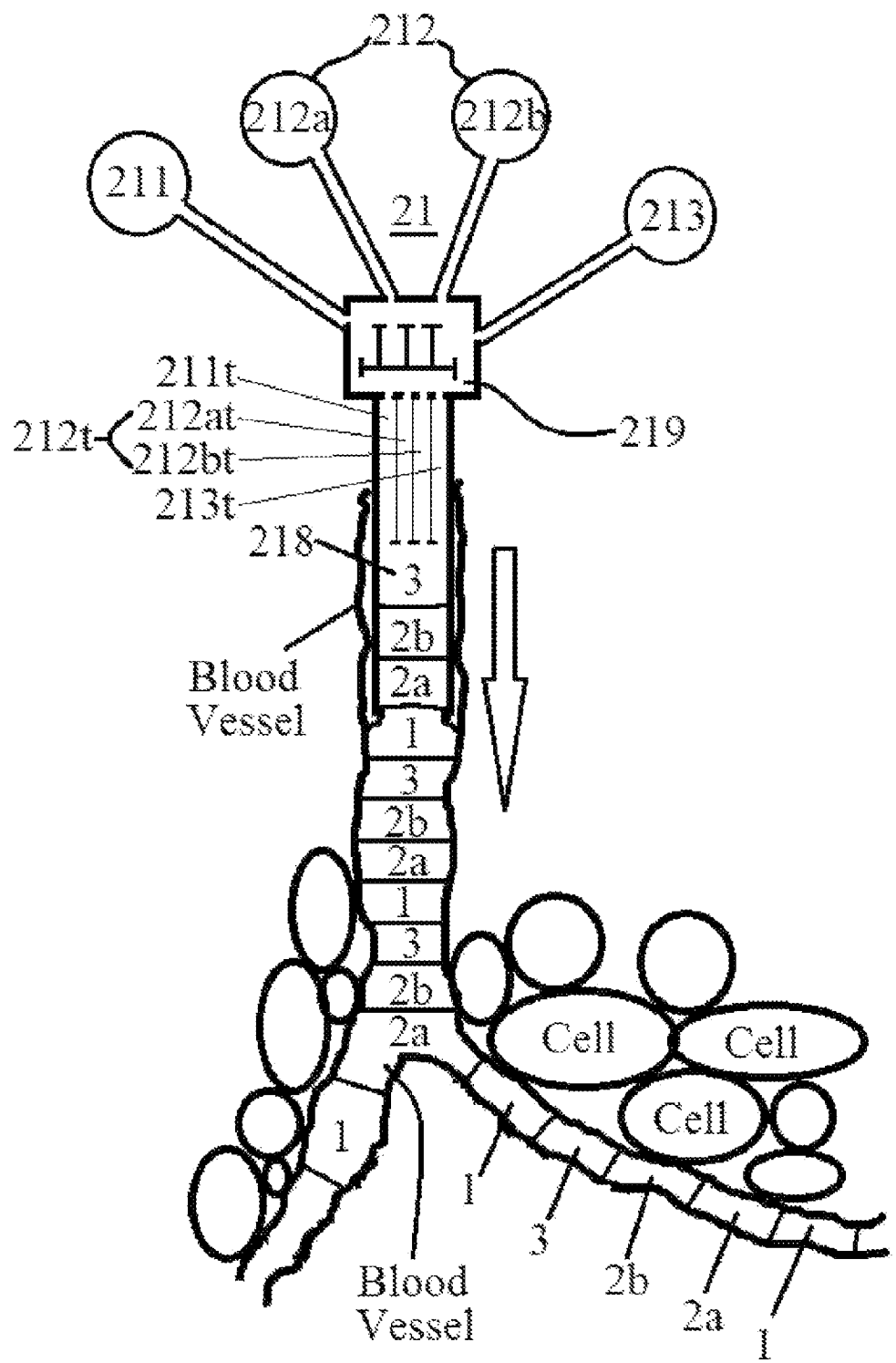
FIG. 3 schematically illustrates a second design of a medical apparatus for assembling and delivering the train-like pharmaceutical composition into a blood vessel lumen in accordance with an exemplary embodiment of the present invention.
Figure 4:
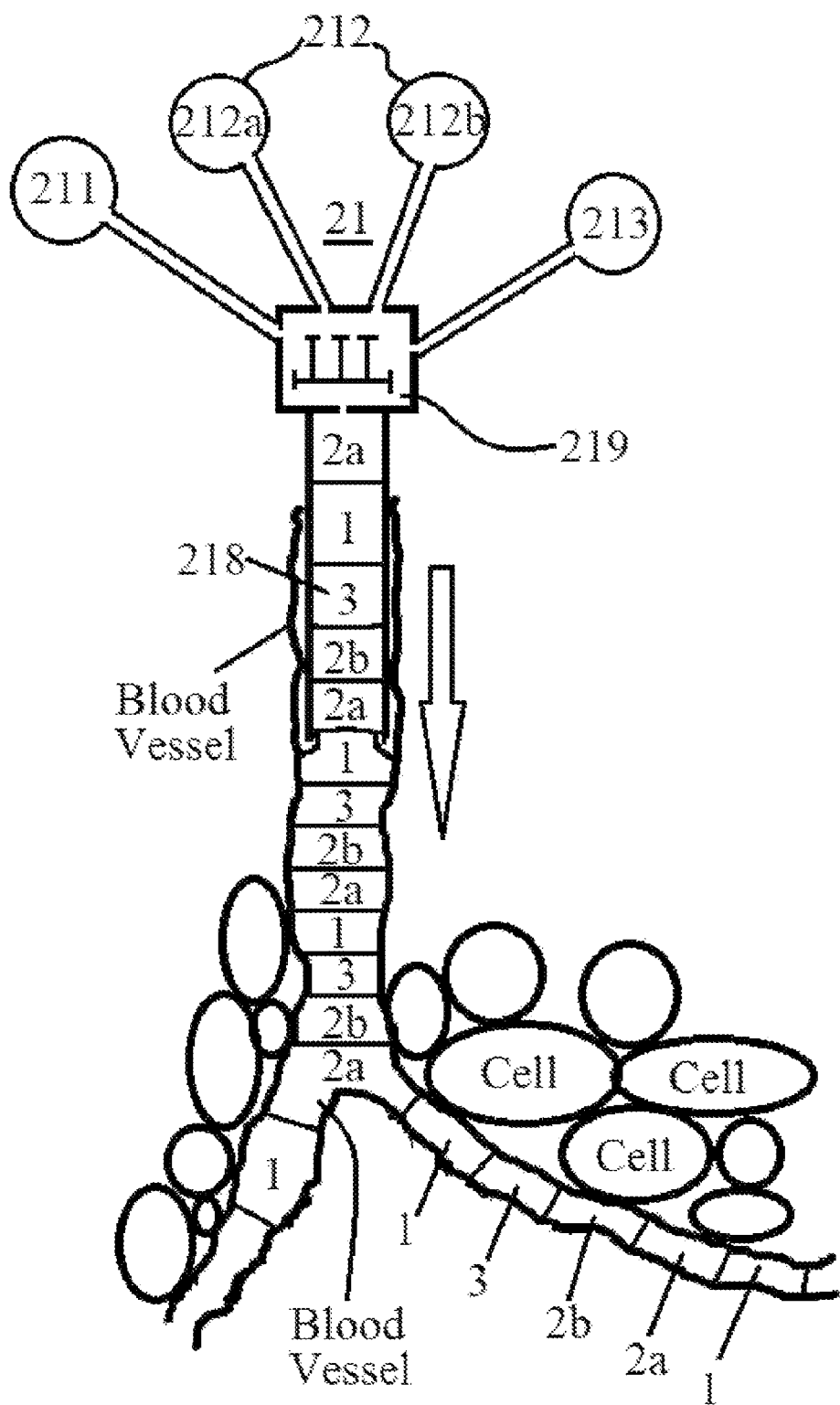
FIG. 4 schematically illustrates a third design of a medical apparatus for assembling and delivering the train-like pharmaceutical composition into a blood vessel lumen in accordance with an exemplary embodiment of the present invention.

The design of medical apparatus 21 as shown in FIG. 2 may be slightly changed. Referring to FIG. 3, a master catheter 218 is inserted into the blood vessel lumen. The head material tube 211t is connected to the master catheter 218 so that the head segment material 1 from said head segment material source 211 is delivered into the blood vessel lumen through the master catheter 218. Similarly, body material tubes and tail material tube (212at, 212bt and 213t) are connected to the master catheter 218 so that the body segment materials 2a, 2b and tail segment material 3 from their sources 212a, 212b and 213 are delivered into the blood vessel lumen through the master catheter 218, The design of medical apparatus 21 as shown in FIG. 3 may also be changed. Referring to FIG. 4, some or all of head material tube 211t, body material tubes 212at, 212bt and tail material tube 213t can be removed from the device. The train configuration will be formed once the materials 1, 2a, 2b and 3 enter the master catheter 218.

Figure 5:
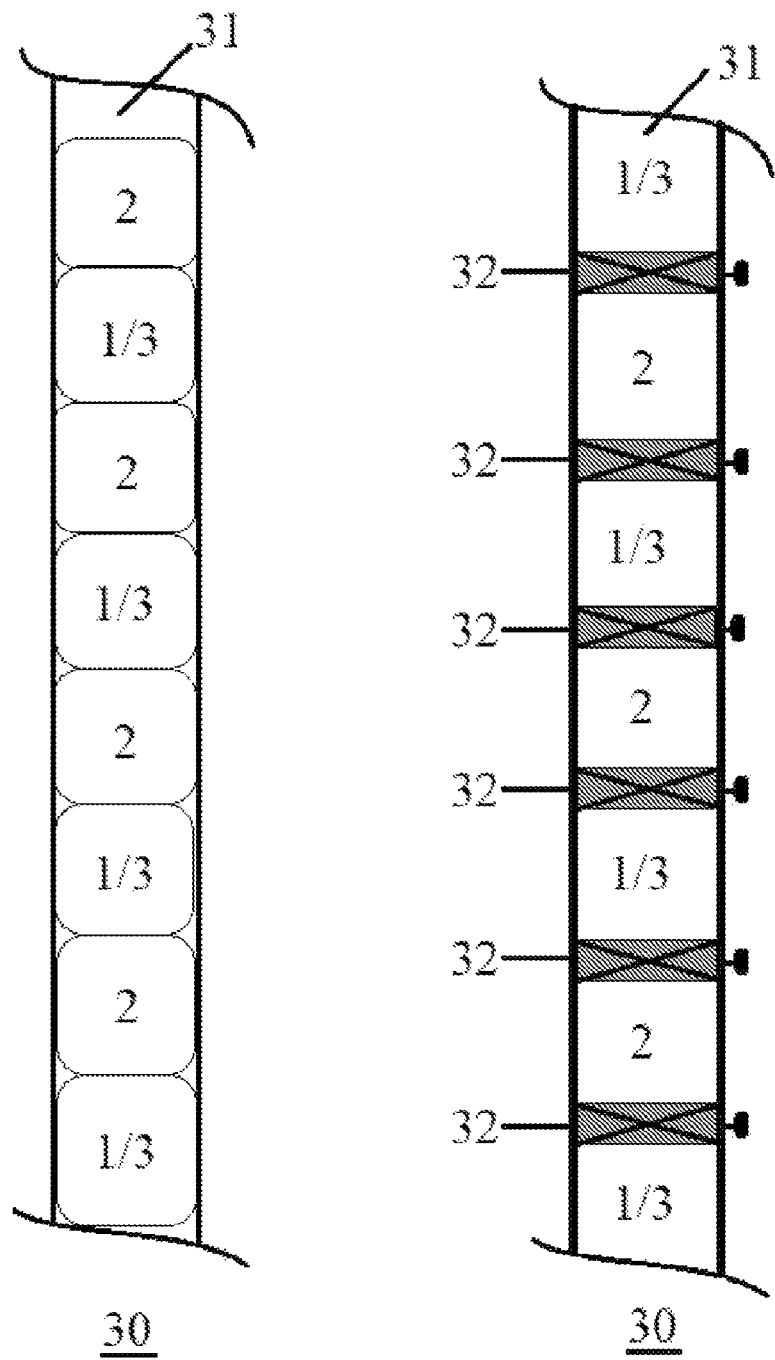
FIG. 5 schematically shows two designs of medical storage device comprising a tube for storing the train-like pharmaceutical composition in accordance with an exemplary embodiment of the present invention.

Referring to FIG. 5, a medical storage device 30 includes a tube 31 (soft or rigid, straight or curved) for sealing and storing the train-like pharmaceutical composition as described above. In some embodiments, storage device 30 includes one or more valves 32 located between the head/tail segment 1/3 and the body segment 2 and separating the head/tail segment 1/3 and the body segment 2 from each other. In the storage of the pharmaceutical composition, the valves 32 may remain closed. When needed, the valves 32 may be automatically or manually opened, and a pressure may be applied at one end of the tube under control, forcing the train-like pharmaceutical composition to exit from the tube 31 at another end, and enter into the lumen of a catheter or a blood vessel.

Figure 6:
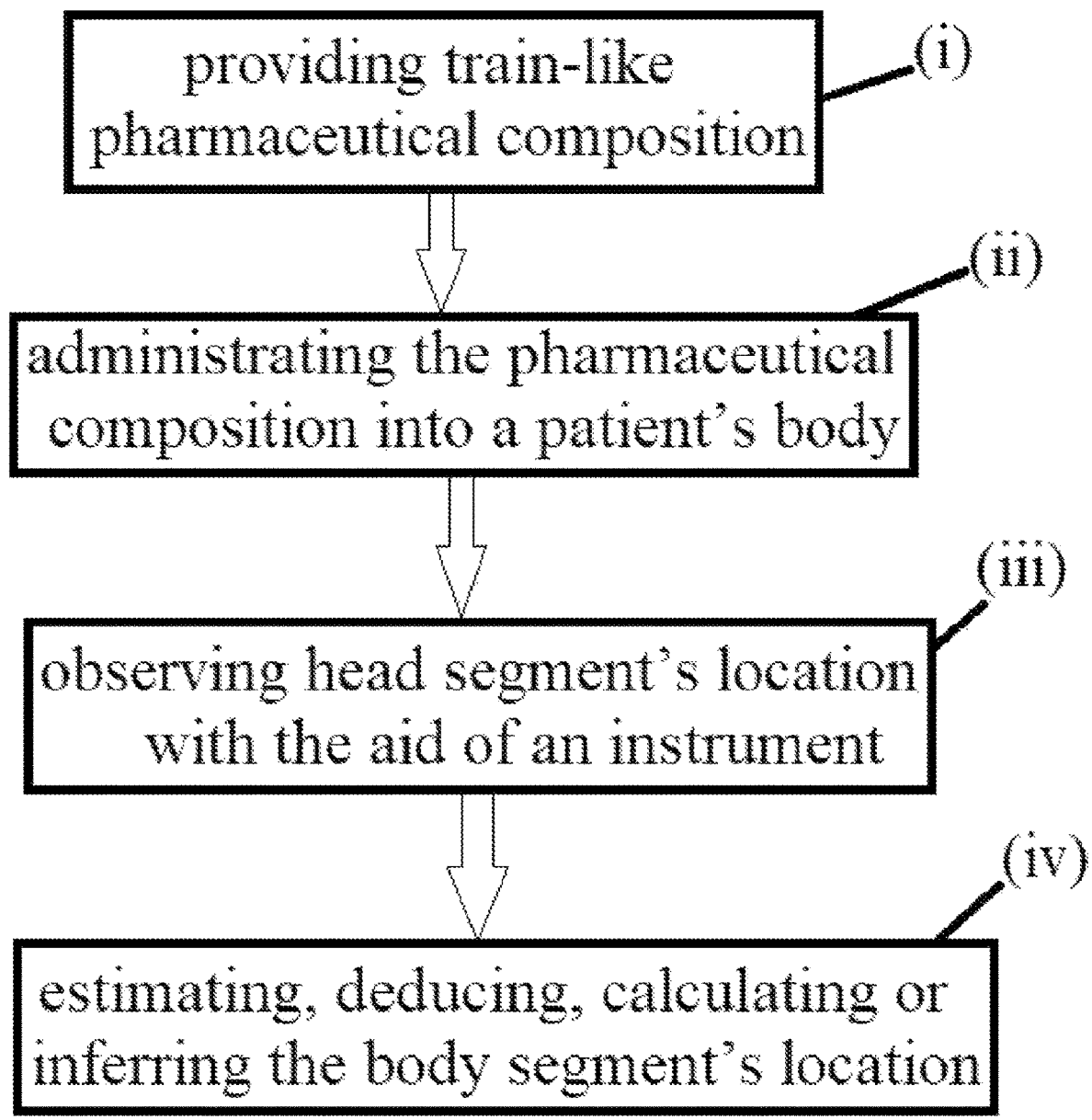
FIG. 6 schematically illustrates a method of treating a blood vessel and cells around the blood vessel in accordance with an exemplary embodiment of the present invention.

As shown in FIG. 6, the invention provides a method of treating a blood vessel and cells around the blood vessel. The method comprises (i) providing, the train-like pharmaceutical composition as described above; (ii) administrating the pharmaceutical composition into a patient's body; (iii) observing the head segment's location with the aid of an instrument; and (iv) estimating, deducing, calculating or inferring the body segment's location based on the observed head segment's location, wherein the body segment's location cannot be directly observed by a human with the aid of the same instrument.

In the foregoing specification, embodiments of the present invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicant to be the scope of the invention, is the literal and equivalent scope of the set of claims that issue from this application, in the specific form in which such claims issue, including any subsequent correction.

The invention claimed is:

1. A method of treating a blood vessel and cells around the blood vessels comprising:
 (i) providing a pharmaceutical composition comprising a head segment and a body segment linearly arranged in series,
  wherein, when the pharmaceutical composition is administrated into a patient's body, the head segment's location can be observed by a human with aid of an instrument; the body segment's location cannot be observed by a human with the aid of said instrument, but it can be deduced from the observed head segment's location; and
  comprises a tail segment that can be observed by a human with the aid of said instrument, wherein the body segment is sandwiched between the head segment and the tail segment, wherein the head segment, the body segment and the tail segment are linearly arranged in series, and wherein the body segment's location can be deduced from the observed head segment's location and tail segment's location,
  wherein the body segment is a liquid alcohol; the head segment is carbon dioxide; and the tail segment is a carbon dioxide, (ii) administering the pharmaceutical composition into a patient's body;
(iii) observing the head segment's location with the aid of an instrument;
wherein the instrument is an X-ray-based imaging apparatus, an ultrasound apparatus, a magnetic resonance imaging (MRI) apparatus, or any combination thereof, and
(iv) estimating, deducing, calculating or inferring the body segment's location based on the observed head segment's location, wherein the body segment's location cannot be directly observed by a human with the aid of the same instrument.

2. The method according to claim 1, wherein the head segment and the body segment arrangement is repeated one or more times.

3. The method according to claim 1, wherein the pharmaceutical composition is confined within a lumen of a tubular structure having an elongation direction.

4. The method according to claim 3, wherein the lumen has an internal diameter at a position of the lumen, and any segment that is confined at said position has a diameter that is the same as said internal diameter.

5. The method according to claim 3, wherein the tubular structure is a blood vessel of a human or an animal, a catheter, or a combination thereof, wherein said combination is defined as the catheter being inserted into the blood vessel and theft lumens being connected, joined, or combined.

6. The method according to claim 1, wherein the X-ray-based imaging apparatus is used in computed tomography (CT), radiography, fluoroscopy, or any combination thereof; and the blood vessel is an arteriole, or the blood vessel is between an arteriole and its downstream capillaries supplying blood to target cells such as tumor cells.

7. The method according to claim 1, wherein the liquid is ethanol.

8. The method according to claim 7, wherein a therapeutic agent is dissolved, suspended, or dispersed in the ethanol.

9. The method according to claim 8, wherein the therapeutic agent comprises a basic substance.

10. The method according to claim 9, wherein the basic substance comprises sodium ethoxide, sodium carbonate, sodium hydrogen carbonate, sodium hydroxide, potassium ethoxide, potassium carbonate, potassium hydrogen carbonate, potassium hydroxide, primary amine, secondary amine, tertiary amine, aliphatic amine, aromatic amine, or any mixture thereof.

11. The method according to claim 7, wherein the ethanol contains less than 0.1% by weight of water, and has a volume of 0.0001-1 milliliter.

* * * * *